US012758205B2

(12) United States Patent
Morgenstern De Muller et al.

(10) Patent No.: US 12,758,205 B2
(45) Date of Patent: Oct. 13, 2026

(54) DILATOR FOR SPINAL SURGERY

(71) Applicants: HOOGLAND SPINE PRODUCTS GMBH, Unterfoehring (DE); Christian Rudolf Morgenstern De Muller, Esplugues de Llobregat (ES); Rudolf Morgenstern Lopez, Esplugues de Llobregat (ES)

(72) Inventors: Christian Rudolf Morgenstern De Muller, Esplugues de Llobregat (ES); Rudolf Morgenstern Lopez, Esplugues de Llobregat (ES)

(73) Assignees: Hoogland Spine Products GmbH, Unterfoehring (DE); Christian Rudolf Morgenstern De Muller, Barcelona (ES); Rudolf Morgenstern Lopez, Barcelona (ES)

( * ) Notice: Subject to any disclaimer, the term of this patent is extended or adjusted under 35 U.S.C. 154(b) by 0 days.

(21) Appl. No.: 18/834,975

(22) PCT Filed: Feb. 7, 2023

(86) PCT No.: PCT/ES2023/070066

§ 371 (c)(1),
(2) Date: Jul. 31, 2024

(87) PCT Pub. No.: WO2023/148423

PCT Pub. Date: Aug. 10, 2023

(65) Prior Publication Data

US 2025/0152159 A1 May 15, 2025

(30) Foreign Application Priority Data

Feb. 7, 2022 (EP) .................................... 22382099

(51) Int. Cl.
*A61B 17/02* (2006.01)

(52) U.S. Cl.
CPC .... *A61B 17/025* (2013.01); *A61B 2017/0262* (2013.01)

(58) Field of Classification Search
CPC ......... A61B 17/025; A61B 2017/0262; A61M 29/00

(Continued)

(56) References Cited

U.S. PATENT DOCUMENTS 8,864,662 B2 * 10/2014 Grey ...................... A61B 17/02 600/245
9,028,522 B1 5/2015 Prado (Continued)

FOREIGN PATENT DOCUMENTS

EP 2911733 A 9/2015
WO WO 2021/106923 A1 6/2021

OTHER PUBLICATIONS

International Search Report for PCT/ES2023/070066, mailed Apr. 26, 2023; 6 pages.

(Continued)

*Primary Examiner* — Eduardo C Robert
*Assistant Examiner* — David C Comstock
(74) *Attorney, Agent, or Firm* — Knobbe, Martens, Olson & Bear, LLP

(57) ABSTRACT

Dilator for percutaneous spinal surgery which comprises a main elongate dilator body and an elongate shield for protecting the nerve root, the main dilator body and the shield each comprising mutually complementary contact surfaces and in which the main body and the shield define a transverse cross section of the dilator, it being possible for the main body and the shield to slide one relative to the other along an axial axis of the dilator, the dilator also comprising a through-hole for receiving a guide rod, characterised in that said hole is placed eccentrically with respect to a (Continued)

combined transverse cross section of the main body and of the shield.

11 Claims, 17 Drawing Sheets

(58) Field of Classification Search
USPC ....... 600/201, 203, 204, 205, 208, 210, 214, 600/219; 606/90, 191
See application file for complete search history.

(56) References Cited

U.S. PATENT DOCUMENTS

| | | | | |
|---|---|---|---|---|
| 9,662,002 | B2 * | 5/2017 | Liu | A61B 1/00149 |
| 9,795,367 | B1 * | 10/2017 | Lee | A61B 1/32 |
| 2009/0149857 | A1 * | 6/2009 | Culbert | A61B 1/0684 606/191 |
| 2010/0114147 | A1 * | 5/2010 | Biyani | A61B 1/32 600/249 |
| 2012/0010471 | A1 * | 1/2012 | Mire | A61B 17/025 600/210 |
| 2012/0232349 | A1 * | 9/2012 | Perrow | A61B 17/0206 600/201 |
| 2013/0274557 | A1 * | 10/2013 | Bowman | A61B 17/0206 600/208 |
| 2014/0121467 | A1 * | 5/2014 | Vayser | A61B 17/025 600/245 |
| 2015/0094533 | A1 * | 4/2015 | Kleiner | A61B 1/00103 600/210 |
| 2015/0265265 | A1 * | 9/2015 | Hynes | A61B 90/30 600/219 |
| 2016/0120532 | A1 * | 5/2016 | Donald | A61B 17/0293 600/210 |
| 2017/0150955 | A1 * | 6/2017 | Williams | A61B 17/025 |
| 2018/0042735 | A1 | 2/2018 | Schell et al. | |
| 2018/0271513 | A1 | 9/2018 | Perrow et al. | |
| 2021/0015501 | A1 * | 1/2021 | Ries | A61B 17/3417 |
| 2021/0169461 | A1 * | 6/2021 | Fatone | A61B 5/4893 |
| 2021/0186316 | A1 | 6/2021 | Thommen et al. | |
| 2022/0265256 | A1 * | 8/2022 | Villamil | A61F 2/4601 |
| 2022/0409234 | A1 * | 12/2022 | McDermott | A61B 17/3417 |

OTHER PUBLICATIONS

Nagahama et al., "PETLIF (Percutaneous Endoscopic Transforaminal Lumbar Interbody Fusion), a Minimally Invasive Lumbar Interbody Fusion Procedure", Bone Joint Nerve, vol. 9, Issue 4, Oct. 1, 2019, pp. 491-498.

* cited by examiner

DILATOR FOR SPINAL SURGERY

CROSS-REFERENCE TO RELATED APPLICATIONS

This application is the U.S. National Phase under 35. U.S.C. § 371 of International Application PCT/ES2023/070066, filed Feb. 7, 2023, which claims the benefit of the priority of European patent application no. 22382099.4 filed on Feb. 7, 2022, the contents of each of which are incorporated herein by reference in its entirety.

TECHNICAL FIELD

The present disclosure relates to a dilator device for percutaneous spinal surgery with a transforaminal approach, and more specifically to a dilator which comprises a shield for protecting nerve roots coming from the spinal cord. The present disclosure is of particular application to percutaneous operations with a transforaminal approach carried out using the space known as Kambin's triangle, which is positioned in the neural foramen, in order to access the intervertebral disc, including vertebral arthrodesis procedures, although the present disclosure is not necessarily limited to said application. The dilator of the present disclosure creates a space at the Kambin's triangle while protecting the exiting nerve root.

BACKGROUND

Kambin's triangle is an anatomical corridor situated in the neural foramen which can be used to access critical structures in a variety of spinal procedures. Kambin's triangle is known as a safe space for carrying out percutaneous procedures, being a clean access route to the intervertebral disc. It is considered safe because it lacks important vascular and/or neural elements. However, it has the problem that space is limited at some points (8-10 mm) and that it is delimited on one side by an exiting nerve root. In endoscopic and/or percutaneous operations there is therefore a danger of damaging the nerve root, either by involuntary cutting during a cutting operation in an articular process to create more space, or by pressure on the nerve applied by the endoscopic devices (for example, the cannula), which may cause dysaesthesia or inflammation of the nerve. This has limited the viable operations that can be done by an approach via the neural foramen.

Document EP2911733A discloses a dilator unit provided with a shield for the nerve. The object of the shield is to protect the nerve root during percutaneous operations which use the neural foramen as an access route. The unit comprises an elongate dilator shaft and a shield. The transverse cross sections of the shaft and shield are complementary and form a circle. The elongate dilator shaft has the function of placing the shield in position. In use, the unit is positioned in the disc space at the required position and rotated to a point at which the outer surface of the shield is adjacent to the nerve root. At this point, the dilator shaft may be withdrawn, leaving the shield in place. An object pursued in this document consists of allowing a box or cage to be placed in the intervertebral space which prevents damage to the nerve root.

The dilator unit of document EP2911733A has a circular transverse cross section which is formed by the dilator shaft and the shield, which are in contact with one another. The unit has at the centre of its transverse cross section an opening corresponding to a passage for receiving a guide wire or thread. The dilator shaft and the shield come in contact along two planar surfaces perpendicular to one another. The shield has recesses in each of said perpendicular planar surfaces. Corresponding projections of the dilator shaft are arranged in said recesses. The arrangement of the perpendicular surfaces and the consequent perpendicular arrangement of the recesses allows shaft and shield to slide along the longitudinal or axial axis of the unit, but any movement in another direction is prevented, and both elements are therefore interlocked. The outer surface of the shield occupies approximately 200° of the 360° of the outer circumference of the unit.

A problem with this device of document EP2911733A is that it does not leave enough space to be able to operate afterwards, as the shield significantly reduces the space once positioned. This reduction in space still limits the possibilities and, in particular, the introduction of an intervertebral box or cage is not viable. In fact, the present inventor is not aware that said device has been commercialised.

SUMMARY

An object of the present disclosure is to disclose a series of means that allow dilatation of the tissues at a Kambin's triangle during percutaneous spinal surgery with a transforaminal approach having a nerve shield for protecting the nerve root to be placed without having the drawbacks of the prior art.

In particular, the present disclosure discloses a dilator for percutaneous spinal surgery, preferably for creating a space at a Kambin's triangle at percutaneous spinal surgery with a transforaminal approach, which comprises a main elongate dilator body and an elongate shield for protecting the nerve root, the main dilator body and the shield each comprising mutually complementary contact surfaces and in which the main body and the shield define a peripheral surface of the dilator in such a way that main body and shield define a transverse cross section of the dilator, it being possible for the main body and the shield to slide one relative to the other along an axial axis of the dilator, the dilator also comprising a through-hole for receiving a guide wire, in which said hole is placed eccentrically with respect to a combined transverse cross section of the main body and of the shield.

The eccentric placement of the hole allows, after the removal of the main body, a guide cable to be used which had been housed in said hole in order to carry out bone cutting operations without having to move or apply pressure to the shield, which could cause damage to the nerve root. Preferably, the hole is placed eccentrically with respect to the cross section of the main body.

The present disclosure also discloses a dilator for percutaneous spinal surgery, preferably for creating a space at a Kambin's triangle at percutaneous spinal surgery with a transforaminal approach, which comprises a main elongate dilator body and an elongate shield for protecting the nerve root, the main dilator body and the shield each comprising mutually complementary contact surfaces and in which the main body and the shield define a peripheral surface of the dilator in such a way that main body and shield define a transverse cross section of the dilator, it being possible for the main body and the shield to slide one relative to the other along an axial axis of the dilator, the dilator also comprising a through-hole for receiving a guide rod, in which the transverse cross section of the dilator is oblong or elongate in shape, the shield being arranged on one of the elongate faces of the transverse cross section.

The elongate shape combined with the eccentric arrangement of the hole allows for a shield which protects more space and which is not inserted excessively into Kambin's triangle, as this reduces the space that is subsequently available.

The present disclosure also discloses a dilator for percutaneous spinal surgery, preferably for creating a space at a Kambin's triangle at percutaneous spinal surgery with a transforaminal approach, which comprises a main elongate dilator body and an elongate shield for protecting the nerve root, the main dilator body and the shield each comprising mutually complementary contact surfaces and in which the main body and the shield define a peripheral surface of the dilator in such a way that main body and shield define a transverse cross section of the dilator, it being possible for the main body and the shield to slide one relative to the other along an axial axis of the dilator, the dilator also comprising a through-hole for receiving a guide rod, in which the shield has a laminar or curved laminar shape.

The laminar shape avoids the presence of elements of the shield which are introduced into the available operating space.

Said features (eccentricity of the guide hole, oblong shape of the dilator and laminar shape of the shield) may be implemented individually in dilators, combined in pairs or all three combined together.

Preferably, the main body is elongate in transverse cross section, the shield being arranged on one of the elongate sides of the transverse cross section. Also preferably, the main body has an equal or large dimension than the shield along a main axis of the elongate or oblong section of the dilator, more preferably the main axis is the larger axis of the elongate or oblong section. More preferably, the main body has larger dimensions than the shield along two main axes of the elongate or oblong section of the dilator, said main axes being perpendicular to each other. This allows for less space being occupied by the nerve shield, which space would reduce the space that is subsequently available.

According to the present disclosure, the main body and shield do not need to be interlocked so as to only be able to slide in respect to one another in the axial direction. Preferably, the shield has no recesses for interlocking with the main body. This allows a slimmer shield to be obtained which therefore occupies less space. In addition, preferably, the shield also has no projections for interlocking. If it is decided to produce recesses or projections for interlocking between the main body and the shield, it is preferable to produce said recesses and projections at each end of the transverse cross section of the shield, thus leaving the central portion free and therefore affecting the thickness, which should preferably be the minimum possible, of the shield as little as possible. Preferably, the main body is monolithic in cross section, not having parts that can slide relative to each other along the longitudinal direction of the dilator.

According to the present disclosure, both shield and main body may have retention means to restrict—but not prevent—movement between shield and main body in a radial direction, said retention means being situated at both ends of the transverse cross section of the shield and which preferably comprise the shape of said ends which preferably have a curved shape. In this case, the retention means restrict movement by providing a resistance which can be overcome.

As it is apparent from the above, the present disclosure discloses a dilator which is advantageous for the dilation of tissues at a Kambin's triangle. For this reason, the dimensions of the transverse cross section of the dilator should be such that it can pass through a human Kambin's triangle. For this, preferably, in some embodiments, the transverse cross section of the dilator may be approximately 9 mm or less on a long axis and 5.5 mm or less along an axis perpendicular to said long axis.

The present disclosure also discloses kits of tools for performing a spinal surgery, preferably with a transforaminal approach, which comprise a dilator according to the present disclosure. The kit may also comprise a drill bit, or various drill bits of different diameters. The kit may also comprise a guide cable, for example a so-called "K-wire". The kit may also comprise known elements of transforaminal access systems, such as Tom Shidi needles (for example with a blunt tip, and/or a cutting tip and/or a drill) and controls for the various transcutaneous components.

The dilator according to the present disclosure may be used in various transcutaneous spinal operations with a transforaminal approach, including vertebral arthrodesis in general and with the installation of intervertebral box(es) or cage(s) in particular. Preferably, the dilator according to the present disclosure may be used in operations that involve cutting a portion of bone (typically from the articular process) to access the disc space. A typical sequence consists of inserting a guide cable, inserting the dilator along the guide cable and removing the main body of the dilator while leaving the shield. In this way the nerve root remains protected. Then additional spine surgery operations may be carried out using the space generated by the dilator, such as anyone of the group comprising bone cutting using a drill bit, cleaning and preparing the disc space and positioning and installing an intervertebral box/cage for arthrodesis, or a combination thereof, preferably in a sequential manner.

BRIEF DESCRIPTION OF THE DRAWINGS

For a better understanding, drawings are attached which show, as an example, an explanatory but non-limiting embodiment of the object of the present disclosure.

DETAILED DESCRIPTION

Figure 3:
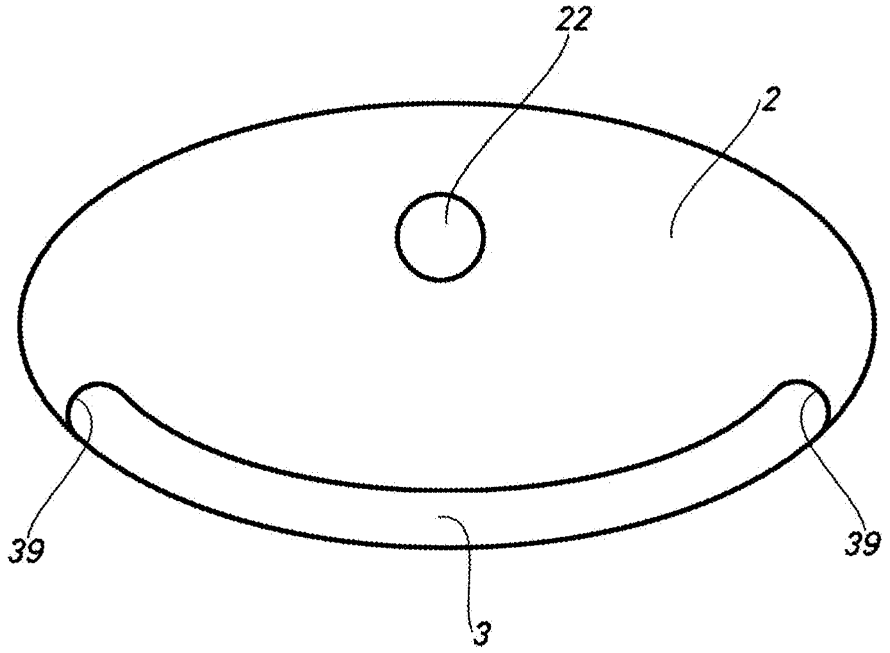
FIG. 3 is a medial cross section of the dilator.
Figure 4:
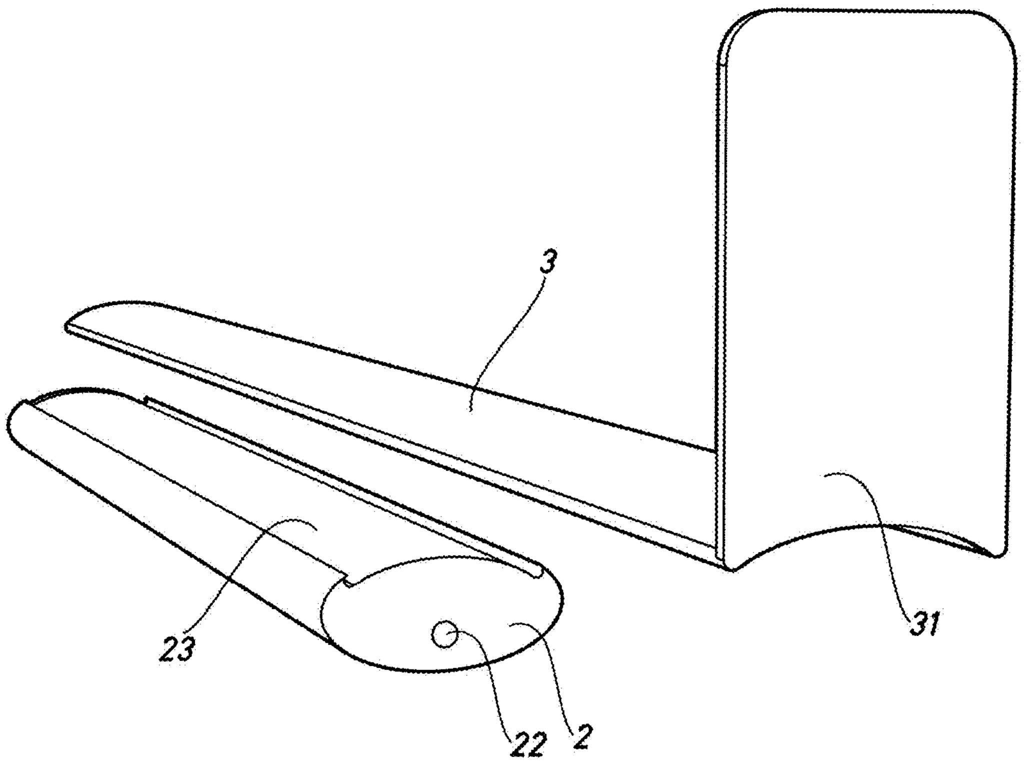
FIG. 4 is another perspective view of the dilator, with the constituent parts thereof separated.
Figure 5:
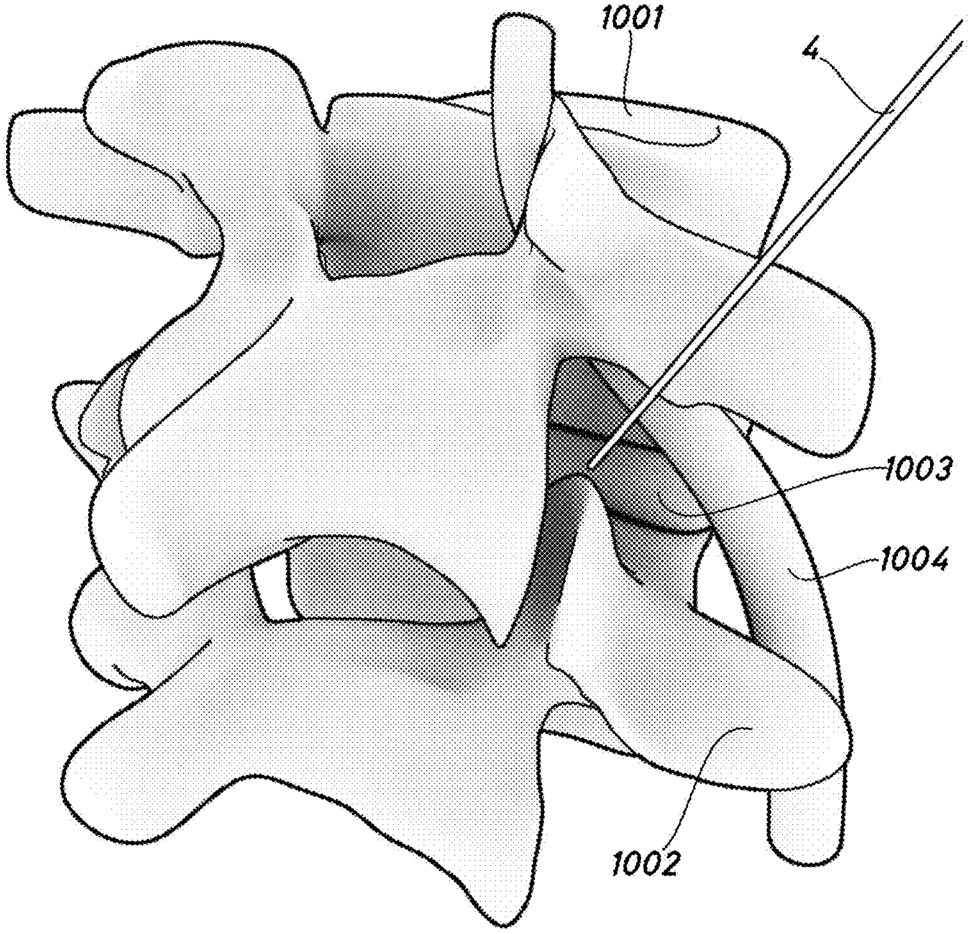
FIGS. 5 to 11 show diagrammatically a method of placing an intervertebral box or cage using the dilator shown in the previous figures.

The dilator 1 is made up of a main body 2 and a shield 3. Both the main body 2 and the shield 3 have an elongate shape for use in percutaneous operations. Main body 2 and shield 3 have conjugate shapes such that the dilator 1 has a uniform outer lateral surface. More specifically, and as can be seen in FIG. 3, the cross section of the dilator 1—made up of the cross sections of the main body 2 and the shield 3—has an elliptical or ovoid shape. The dilator 1 also has a longitudinal through-hole 22, the object of which is to receive a guide (for example a K-wire) which will guide the trajectory of the dilator 1 inside the body of the patient. The hole 22 is situated eccentrically with respect to the centre of the cross section of the dilator. In particular, the hole 22, which is in the main body 2, is situated farther from the outer surface of the dilator 1 formed by the shield 3 than from an outer surface of the dilator 1 formed by the main body. The outer surfaces formed respectively by the main body and the shield are opposite one another. This offsetting of the hole makes it easier subsequently to create additional space by the positioning of a drill bit to cut the bone of one or both vertebrae.

Figure 1:
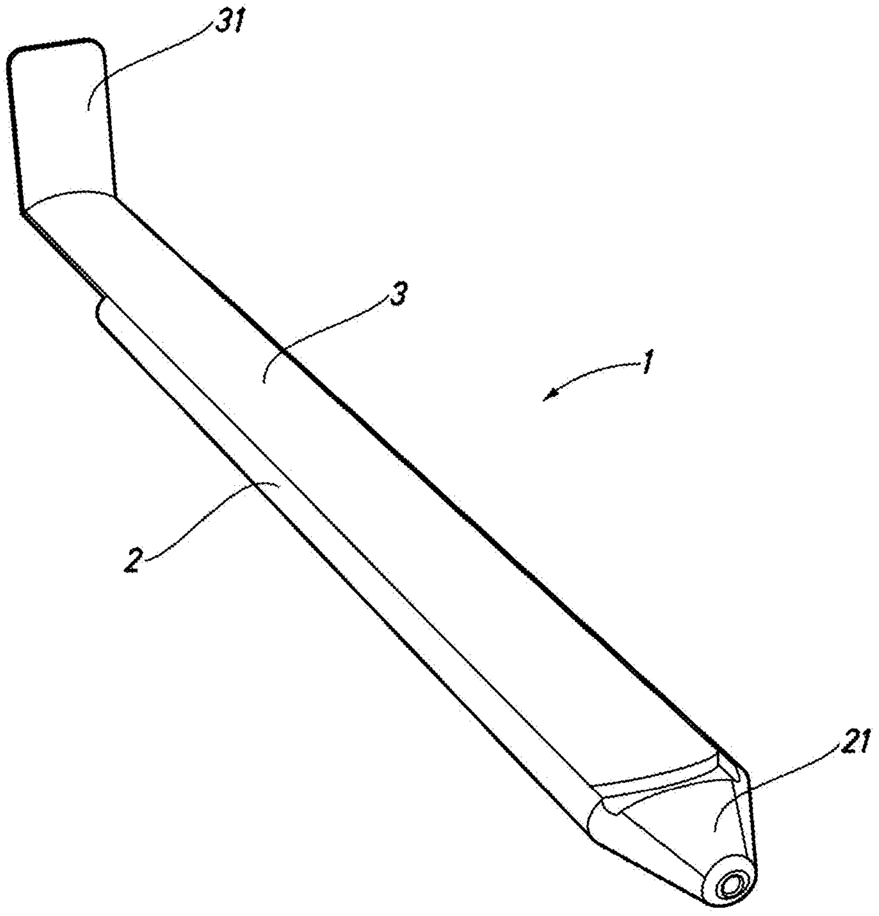
FIG. 1 is a perspective view of a dilator.

The main body 2 also has a pointed distal end 21. As can be seen in FIG. 1, the main body 2 has a recess for receiving the shield, along which the shield can slide. However, it is possible for the main body and the shield not to be interlocked, so that the relative movement in a radial direction may be completely allowed, or not totally prevented.

The shield 3 has a curved laminar shape in cross section. The laminar shape helps achieve a shield that is as slender as possible. More specifically, the shield 3 is formed in cross section by two main surfaces, an outer surface which forms part of the outer surface of the dilator 1, and another inner surface parallel thereto, as well as two ends which form a connection between both main surfaces. For the shield to be more slender, both main surfaces are parallel to one another. In addition, the shield does not have attachment recesses on said main surfaces, which allows for an even more slender shield. In addition, in the case shown, neither do the ends 39 of the shield 3 have recesses for interlocking with the main body. It is not necessary to interlock the main body 2 and the shield 3 to prevent any movement between the two. If thought appropriate, the ends 39 could have projections for interlocking (not shown in the figure) or alternatively could be given a shape that restricts, but does not prevent, movement in a radial direction.

The shield may have a shank 31 for handling. The shank may take various shapes. In general, the instruments have been shown diagrammatically and any necessary connection and/or handling elements may be arranged at the distal and/or proximal ends thereof.

Figure 2:
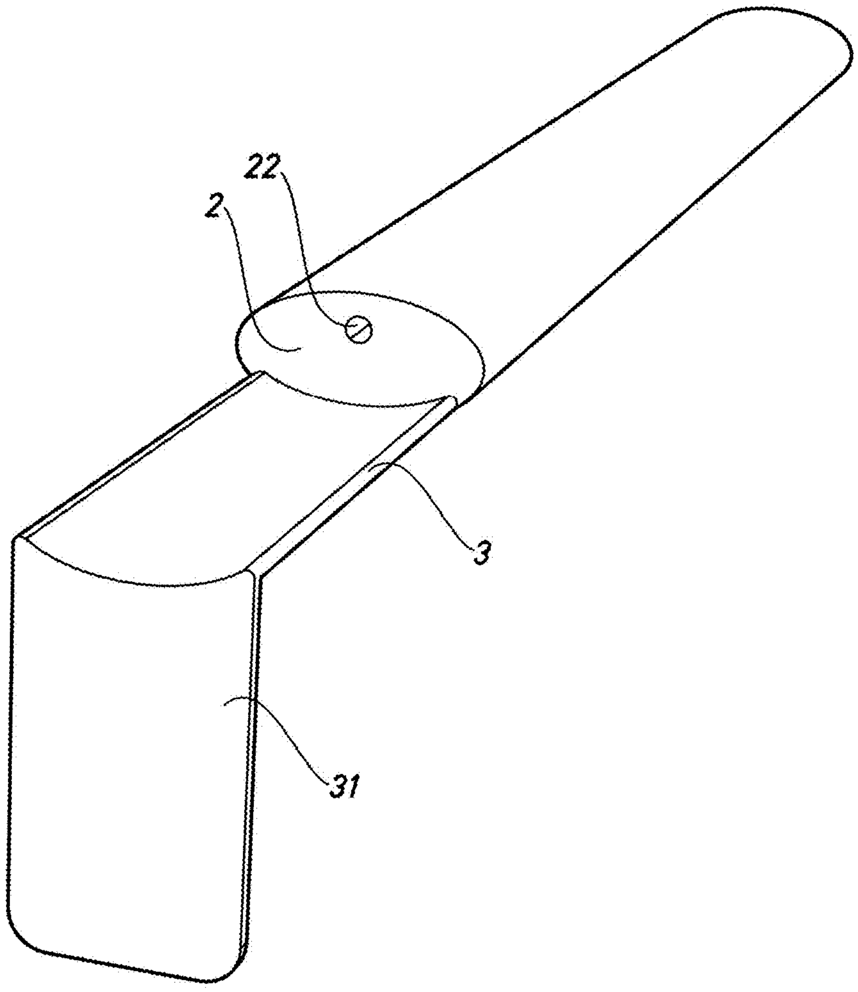
FIG. 2 shows the dilator from a different point of view from that shown in FIG. 1.

As shown diagrammatically in FIG. 2, the box is introduced using percutaneous means. An endoscopic cannula 6 has been shown in FIG. 2 which approaches the intervertebral space by the anterior route.

Figure 6:
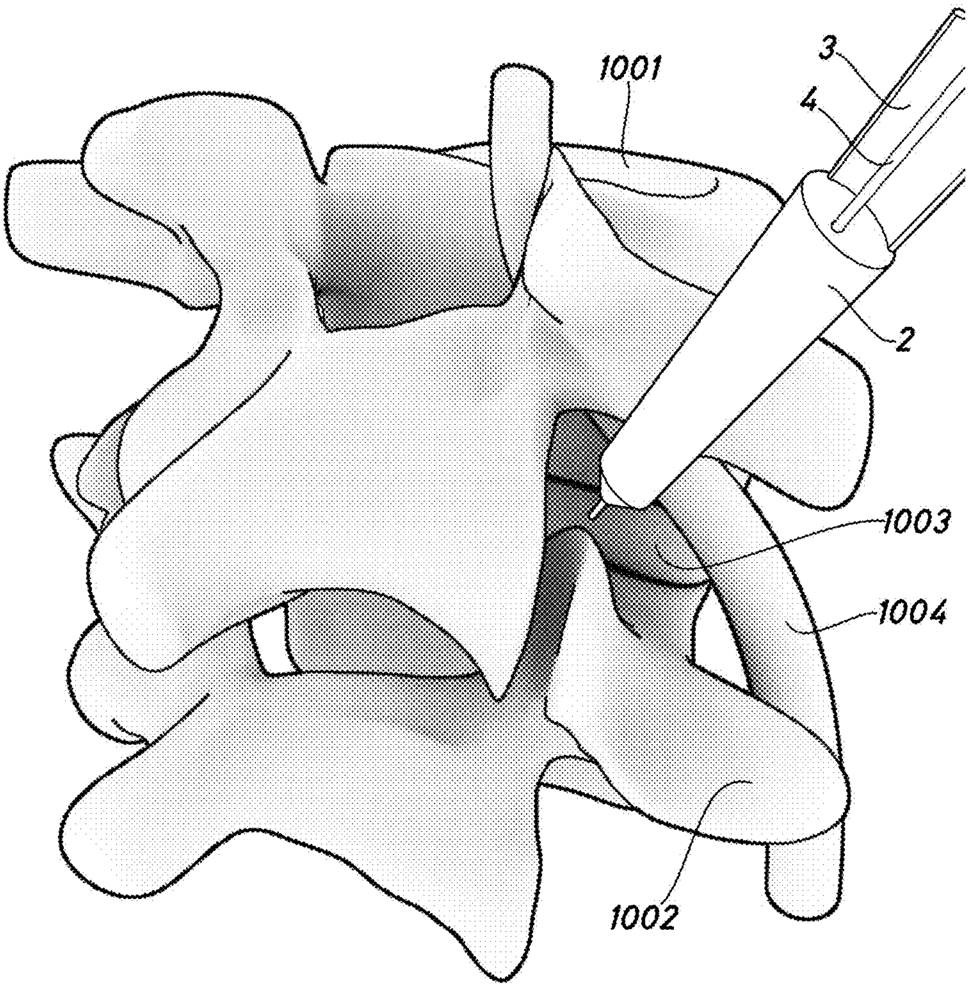
Figure 7:
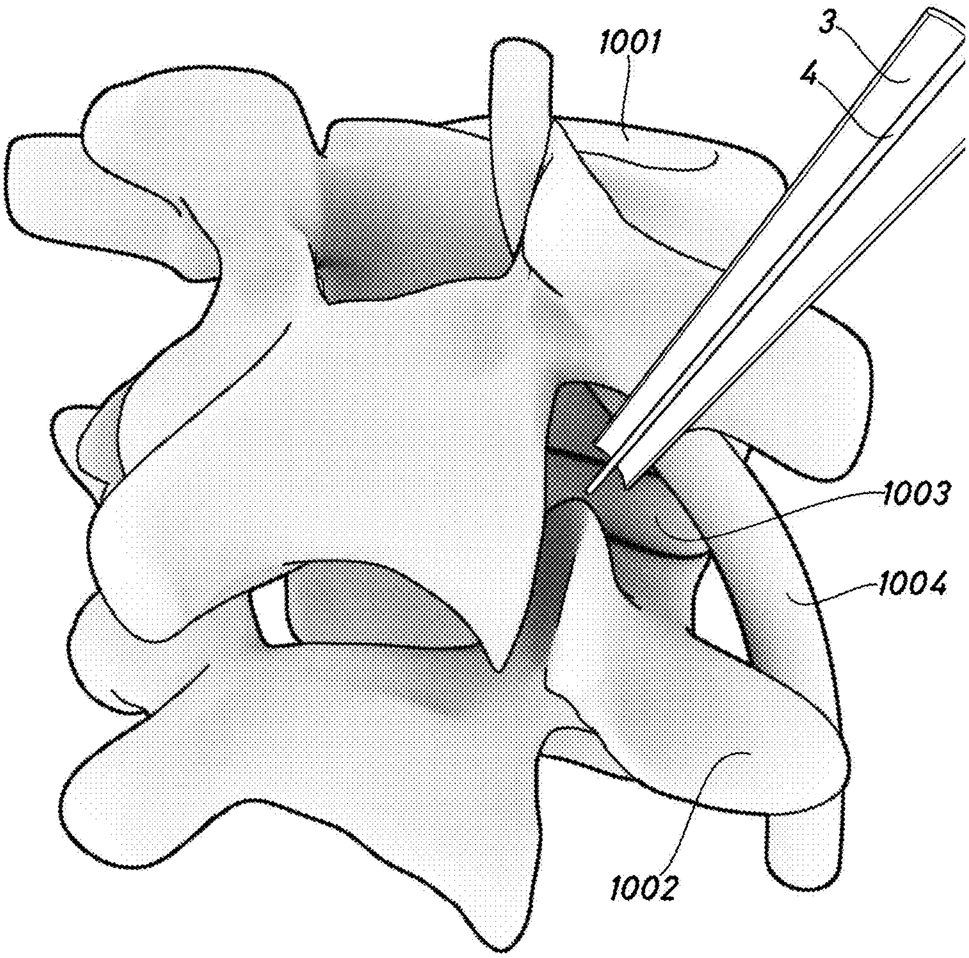
Figure 8:
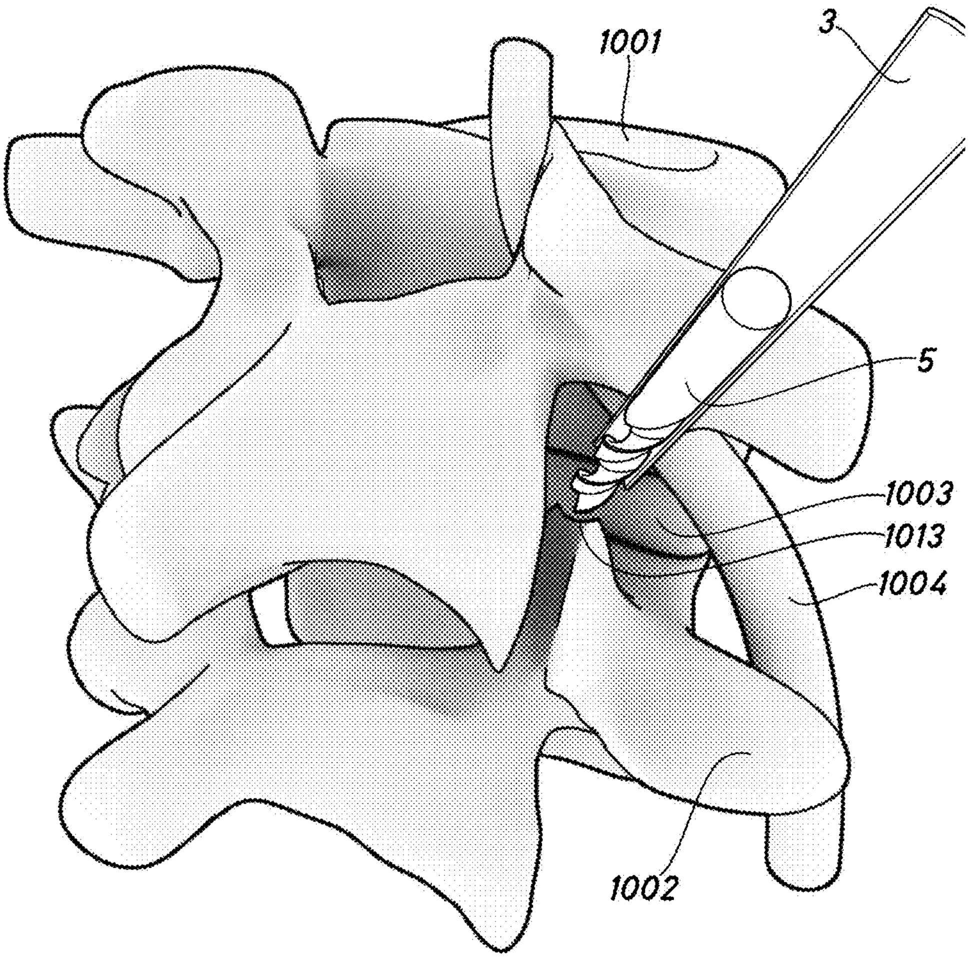
Figure 9:
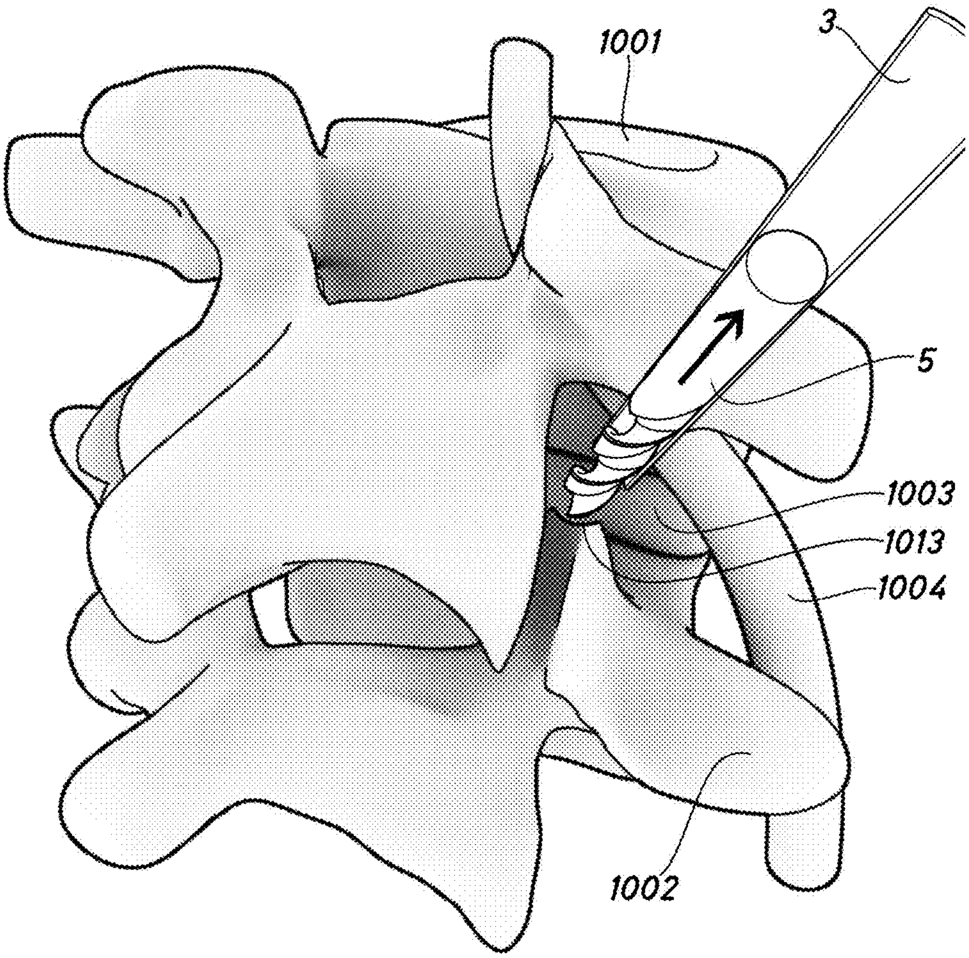
Figure 10:
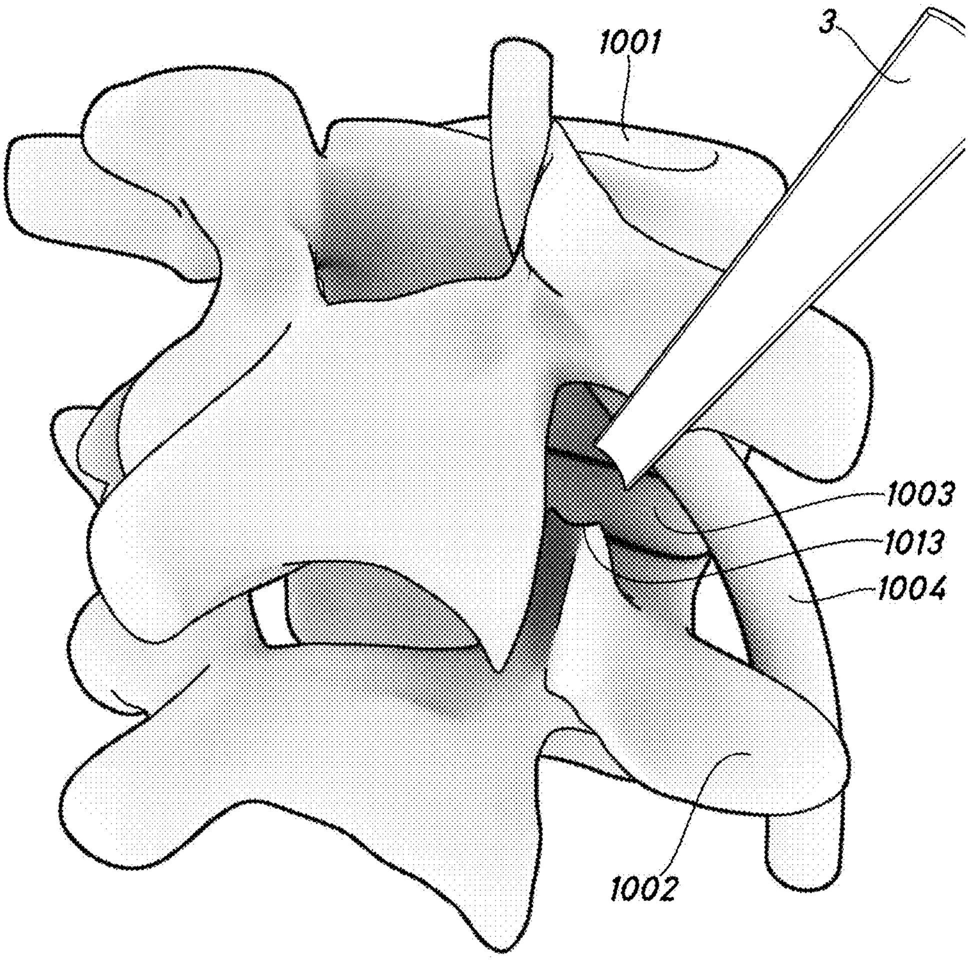
Figure 11:
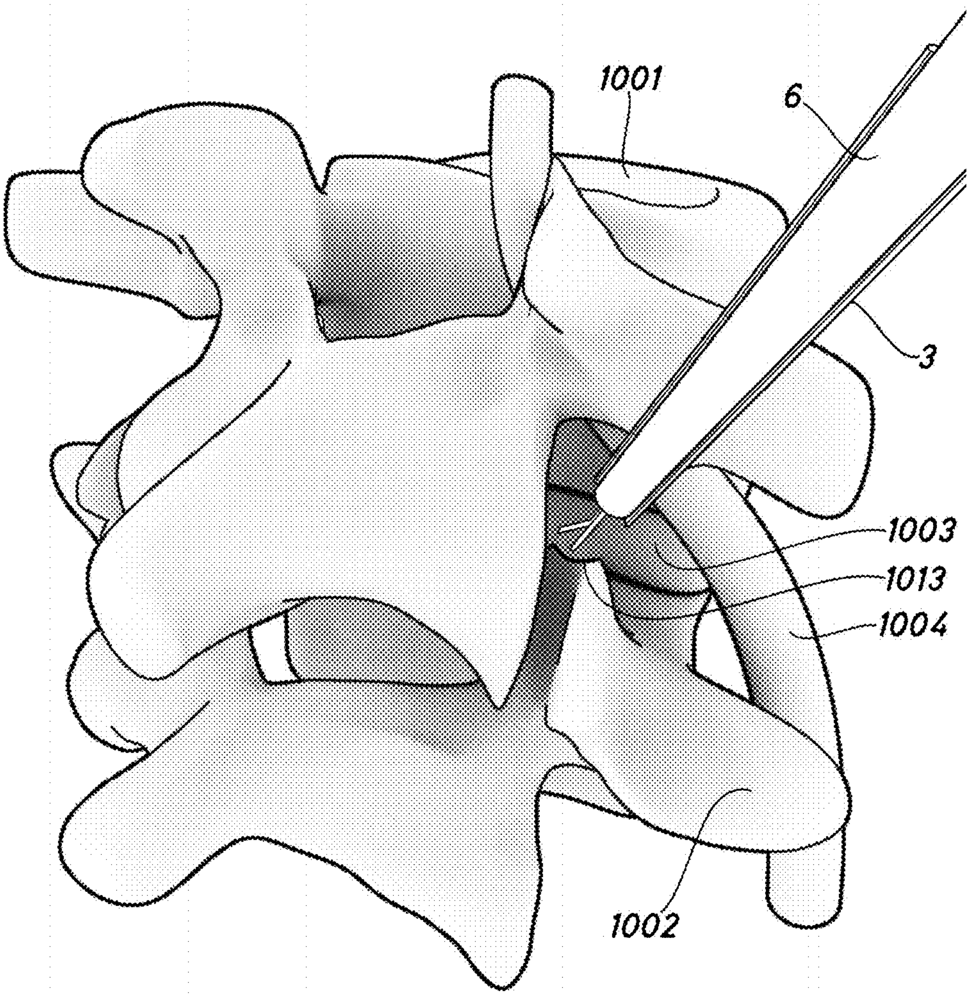
Figure 12:
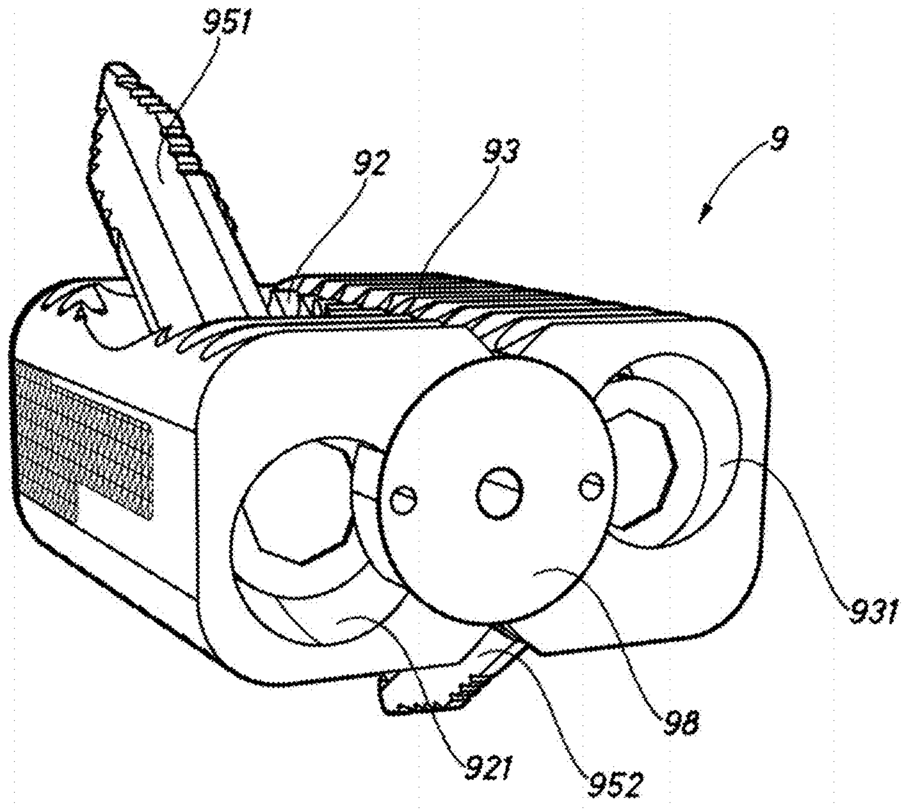
FIG. 12 shows an intervertebral box or cage.
Figure 13:
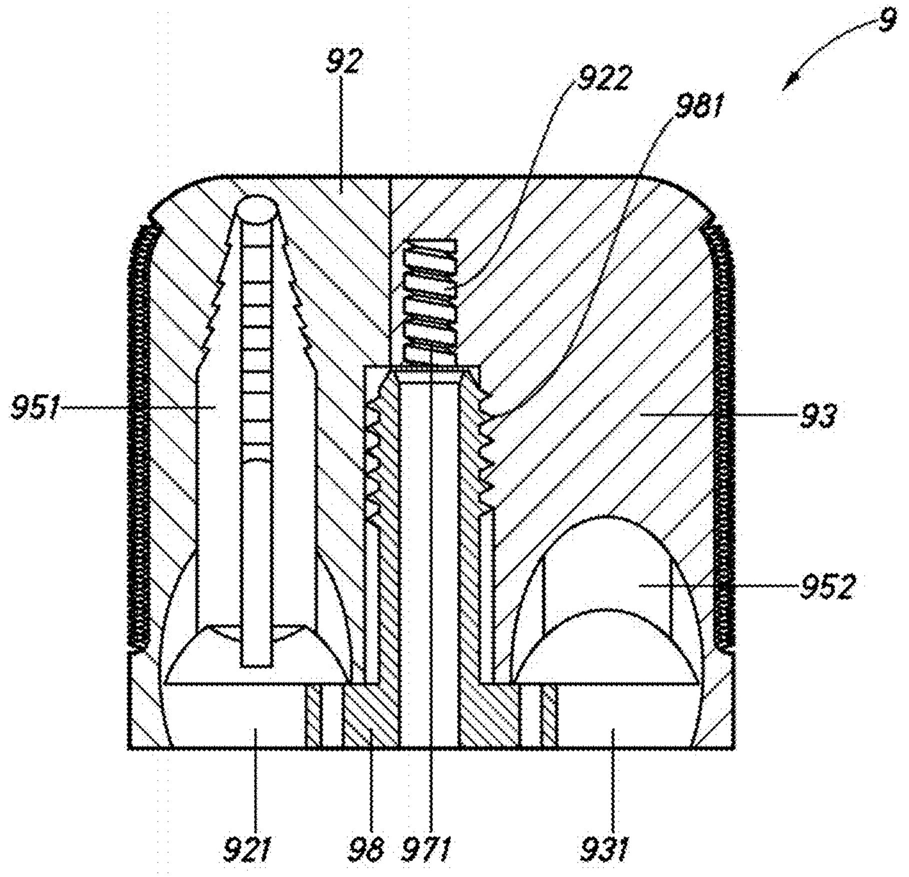
FIG. 13 is a cross section, along a bottom plane of the box in FIG. 12.
Figure 14:
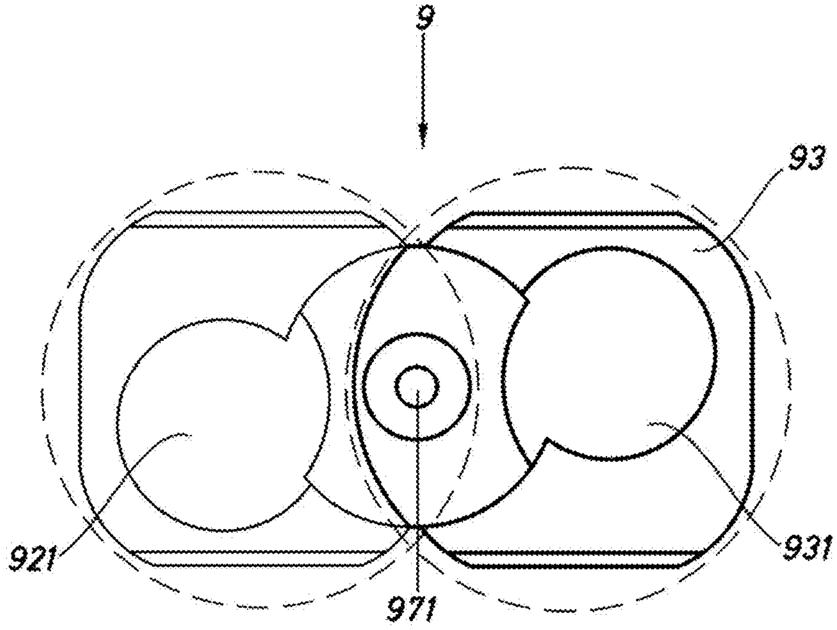
FIG. 14 shows the fitting together of the parts that form the box and the fitting thereof in a cannula.
Figure 15:
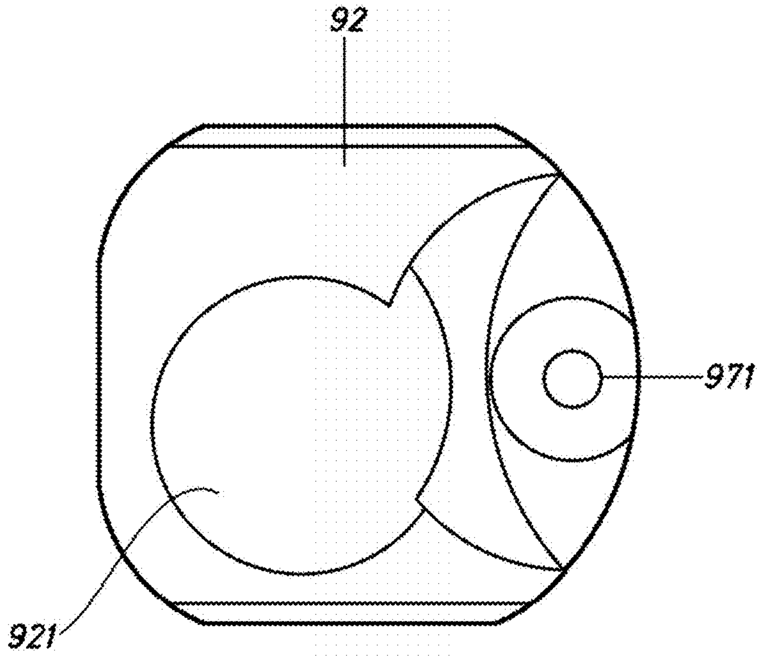
FIG. 15 shows one of the two parts that form the box.

FIGS. 5 to 11 show diagrammatically a procedure for placing the dilator. The method may begin (FIG. 5) by placing a guide cable 4 (K-wire) in position by a transforaminal approach. The guide cable 4 is positioned opposite the intervertebral disc 1003 situated between the vertebrae 1001, 1002 or alternatively penetrates therein. From here, said cable will serve as a guide for introducing the dilator with the corresponding shield 3 thereof facing towards the nerve root 1004 that is to be protected, as shown in FIG. 6. Next, the main body 2 of the dilator is removed, being made to slide with respect to the shield 3, which remains in position, protecting the nerve root 1004. As can be seen in FIG. 7, the guide cable 4 also remains in position. From the arrangement in FIG. 7, the required transepidermal operation by transforaminal approach may begin. FIGS. 8 to 11 show a possible operation. To illustrate the operations, the endoscopic cannula that would protect the elements that are introduced, depending on what is required in each case, has not been shown in the figures. FIG. 8 shows how a drill bit 5 is introduced in order to cut part of the inferior vertebra 1002. It would also be possible to cut part of the superior vertebra, or both vertebrae, depending on requirements. The object of cutting is to gain space for subsequent operations. Since, in order to make the cut, the drill bit has to project from the surrounding cannula (not shown in the figures), the shield 3 acts as a barrier which prevents cutting and/or compression of the nerve root 1004. FIG. 8 shows the cut portion 1013. In this case, the cut portion corresponds to the superior articular process of the inferior vertebra 1002. It will be noted that the fact that the hole in the dilator is in an eccentric position with respect to the centre of the cross section of the dilator facilitates being able to cut part of the vertebra without having to move the shield 3 from its position, as this would result in applying pressure to the nerve root 1004 and causing dysaesthesia.

The drill bit 5 is then removed and it is now possible to carry out the necessary operations. If a considerable amount of bone has to be removed, it is possible to introduce two or more drill bits sequentially using an increasingly large drill bit diameter.

It is then possible to introduce a tool 6 (clamp and/or cutter, extractor, etc.) to clean the interior of the disc 1003, which leaves the way clear to place a cage or box 9 to carry out intervertebral fusion. Using this system, it is possible to introduce percutaneously various types of intervertebral boxes or cages, the object of which is to fuse and/or separate two vertebrae by being interposed in the intervertebral space.

FIGS. 12 to 15 show an example of a box 9 which is made up of two bodies 92, 93 having conjugate shapes. Each of the two bodies 92, 93 is of a suitable size to enter through an endoscopic cannula which passes through Kambin's triangle, for which said body has a corresponding hole 971 for a guide cable. The parts are assembled together.

When the parts are assembled, the guide holes are coaxial, one hole being a through-hole and the other having a thread 922 for receiving the endoscopic guide.

Assembly may be carried out, for example, by means of a set of respective conjugate recesses and projections situated at the contact interface between both parts. Said projections may preferably be perpendicular to the coaxial axis of said holes.

Preferably, said holes are arranged on each of said conjugate projections.

The box also comprises a connection element in the form of a screw 971 which is fixed by means of a thread 981, securing the parts 92, 93. The thread 981 may be fitted into respective threads in one or both parts 92, 93. Each of the two parts 92, 93 has a through-hole 921, 931 which has an inlet in the proximal area and an outlet in one of the bases for receiving a means of fixing to the adjacent vertebrae, for example, the screws or pins 951, 952, which have sharp projections. Each of the sharp pins 951, 952 is arranged on one of the bases of the box, pointing in different directions.

The method of positioning the box 9 may be as follows:

First, a part 92 is positioned, being guided by an endoscopic guide which is threaded onto the corresponding thread 922 of the part 92. Without removing the guide, the other part is positioned through the endoscopic cannula, said part also being guided by the endoscopic guide. This movement causes both parts to be held against one another, interlocking owing to the conjugate shapes thereof.

Next, the pins 951, 952 are inserted, driving said pins into the adjacent vertebrae.

Finally, the screw 98 is slid along the endoscopic guide and then a tool is introduced to thread the screw 98.

Next the threading tool, the endoscopic guide, which is unscrewed, the endoscopic cannula and the shield 3 are removed.

The installation method may be different from the one shown, and it is also possible to use different percutaneous and even non-percutaneous techniques. The order of the operations is also susceptible to changes. The introduction route is through Kambin's triangle made safe by the use of a shield for protecting the nerve root, which is preferably positioned by means of a dilator as shown above.

Figure 16:
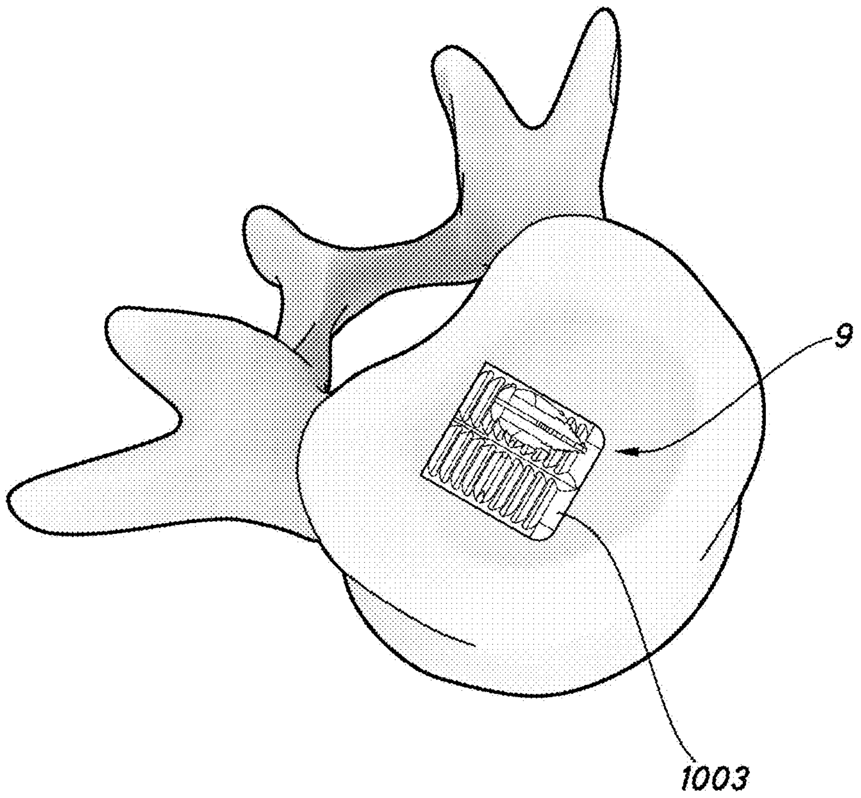
FIG. 16 shows diagrammatically the position of a box or cage in an intervertebral space, after having been placed using a procedure like the one shown in FIGS. 5 to 11.

FIG. 16 shows how the box 9 would be positioned, typically at an angle owing to the transforaminal approach used for introduction thereof. However, in an intervertebral fusion operation typically two boxes 9 will be placed, one through the left neural foramen and the other through the right.

Figure 17:
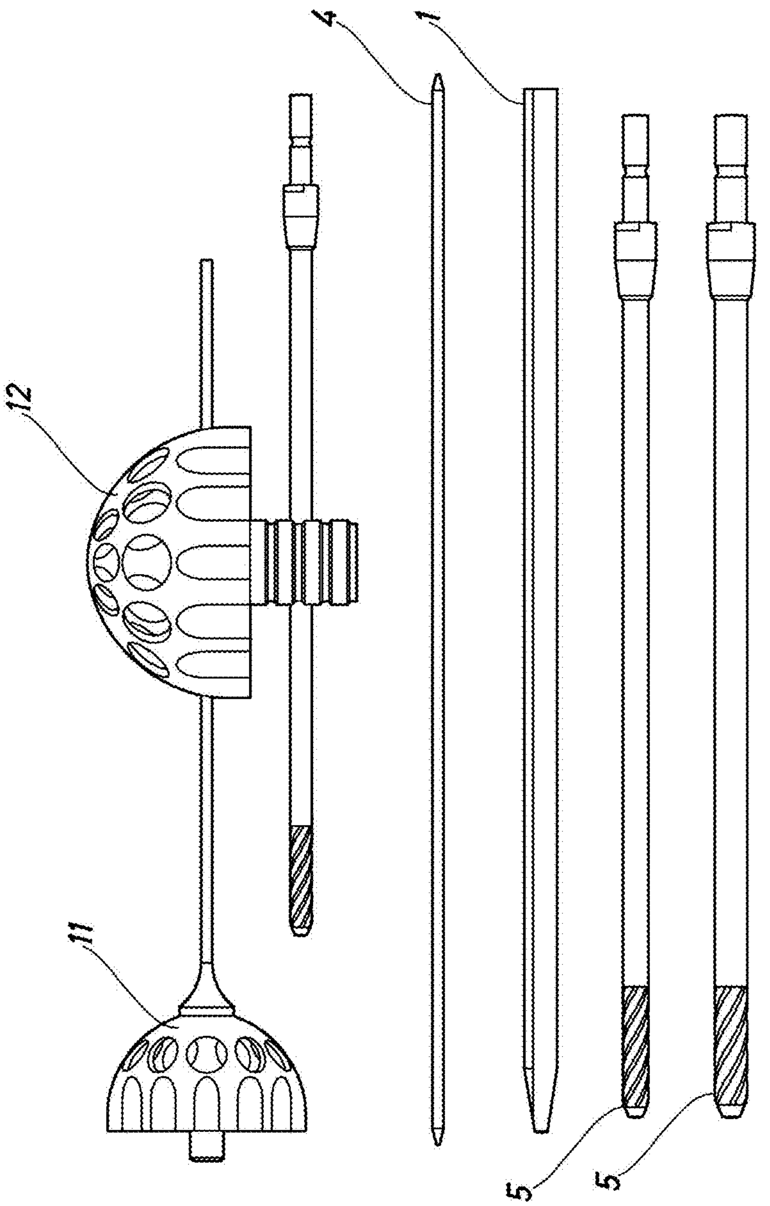
FIG. 17 shows diagrammatically a commercial kit or unit which comprises a dilator like the one in FIGS. 1 to 4.

FIG. 17 shows an example of a marketable kit for carrying out transcutaneous operations which includes a dilator 1 according to the present disclosure, a guide cable 4 and at least one drill bit 5, or a set of drill bits of different sizes. The kit may also comprise known elements of transforaminal access systems, such as Tom Shidi needles 11 (for example with a blunt tip, and/or a cutting tip and/or a drill and controls 12 for the various elements, etc.). In general, the heads for connection to the control of the different elements have not been shown in the figures so as not to complicate the illustrations. Nor has the use of the different endoscopic cannulas, employed as required and according to the judgement of the specialist doctor, been illustrated.

The dimensions of the dilator shown may vary depending on the type of vertebra to which said dilator will be directed. In the example, the transverse cross section of the dilator may be approximately 9 mm on the long axis and 5.5 mm along an axis perpendicular to said long axis. The shield may, for example, have a constant thickness of 0.75 mm and a length of 8 mm measured in the direction of said long axis. The through-hole of the dilator may be approximately 1.75 mm and may be arranged at a distance of at least 2 mm from the shield. The length of the dilator in the axial direction may be approximately 180 mm, and that of the shield, 170 mm.

The installation method may be different from the one shown, and it is also possible to use different percutaneous techniques and modifications to the one shown. The order of the operations is also susceptible to changes.

Although the disclosure has been described with respect to preferred embodiments, these should not be considered to limit the disclosure, which will be defined by the widest interpretation of the following claims.

What is claimed is:

1. A dilator for percutaneous spinal surgery with a transforaminal approach, the dilator comprising:

a main elongate dilator body having an outer portion, the outer portion comprising a recess; and an elongate nerve shield for protecting a nerve root, the shield having a curved laminar shape comprising an inner surface and an outer surface parallel to one another to form a slender body;

the main body and the shield each comprising mutually complementary contact surfaces and in which the main body and the shield define a transverse cross section of the dilator having a continuous elliptical shape, the main body configured to receive the shield in the recess to slide relative to each other along an axial axis of the dilator, the dilator further comprising a through hole enclosed by the main body extending through the dilator for receiving a guide cable, wherein the through hole is placed eccentrically with respect to the transverse cross section of the dilator, and wherein the main body comprises an equal or larger dimension than the shield along the axial axis of the dilator.

2. The dilator according to claim 1, wherein a transverse cross section of the main body is oblong or elongate in shape, the shield being arranged on one of elongate faces of the transverse cross section of the main body.

3. The dilator according to claim 2, wherein said faces have a curved shape.

4. The dilator according to claim 1, wherein a transverse cross section of the shield has a central area of constant thickness.

5. The dilator according to claim 1, wherein the shield has no recesses for interlocking with the main body.

6. The dilator according to claim 1, wherein the shield has no projections for interlocking with the main body.

7. The dilator according to claim 1, wherein both the shield and the main body comprise a retainer to restrict relative movement between the main body and the shield, the retainer of the shield being situated at both ends of a transverse cross section of the shield.

8. The dilator according to claim 7, wherein said retainer of the shield further comprises a shape of both ends which have a curved shape.

9. A kit of tools for percutaneous spinal operations by a transforaminal approach, wherein the kit comprises the dilator according to claim 1.

10. The kit according to claim 9, further comprising a drill bit.

11. The kit according to claim 9, further comprising the guide cable.

* * * * *